United States Patent [19]

Beigler et al.

[11] 4,237,881
[45] Dec. 9, 1980

[54] DEVICE FOR THE INTRAVENOUS OR ENTERIC INFUSION OF LIQUIDS INTO THE HUMAN BODY AT A PREDETERMINED CONSTANT RATE

[75] Inventors: Myron A. Beigler, Los Altos Hills; Hal C. Danby, Palo Alto, both of Calif.

[73] Assignee: Anatros Corporation, Palo Alto, Calif.

[21] Appl. No.: 972,730

[22] Filed: Dec. 26, 1978

[51] Int. Cl.³ .......................... A61M 5/00; A61B 5/02
[52] U.S. Cl. ............................. 128/214 F; 128/205.13
[58] Field of Search ............. 128/214 F, 214 B, 145.6, 128/145.7, DIG. 12, 205.13

[56] References Cited

U.S. PATENT DOCUMENTS

| | | | |
|---|---|---|---|
| T825264 | 10/1969 | Carter | 271/22 |
| 3,291,151 | 12/1966 | Loken | 128/214 B |
| 3,375,824 | 4/1968 | Krakaver et al. | 128/214 F |
| 3,411,502 | 11/1968 | Hofstra et al. | 128/214 B |
| 3,450,134 | 6/1969 | Willgerodt | 128/214 B |
| 3,506,005 | 4/1970 | Gilio et al. | 128/214 F |
| 3,507,278 | 4/1970 | Werding | 128/214 F |
| 3,731,681 | 5/1973 | Blackshear et al. | 128/214 F |
| 3,734,351 | 5/1973 | Gandin | 128/214 F |
| 3,757,776 | 9/1973 | Bauman | 128/145.6 |
| 3,923,053 | 12/1975 | Jansson | 128/145.6 |
| 3,951,147 | 4/1976 | Tucker et al. | 128/214 F |
| 4,033,479 | 5/1977 | Fletcher et al. | 128/214 F |
| 4,041,944 | 8/1977 | Rhodes | 128/214 F |
| 4,062,360 | 12/1977 | Bently | 128/214 B |
| 4,077,405 | 3/1978 | Haerten et al. | 128/214 F |

Primary Examiner—Robert W. Michell
Assistant Examiner—C. W. Shedd
Attorney, Agent, or Firm—Lowhurst & Aine

[57] ABSTRACT

A portable device for accurately metering a liquid for intravenous or enteric infusion into a patient's body in which the pressure from a pressure source is utilized to pressurize the liquid and the pressurized liquid becomes the sole driving force to meter and to infuse the liquid into the body. The pressurized liquid is applied alternately to one of a pair of flexible liquid bladders the other one being connected to a discharge device, such as a tube, so that, as one liquid bladder is filled with pressurized liquid, the other bladder is emptied into the patient. The expanding liquid bladder and the contracting liquid bladder cooperate with a teeter totter type control which applies pressure to the contracting liquid bladder and is damped to control the rate of expansion and contraction. The position of the teeter totter controls the valving for applying pressurized fluid from one side to the opposite by alternatively selecting channels of fluid flow to each liquid bladder. The angular motion of the teeter totter is controlled by a pair of flexible damping bladders connected through an adjustable constant flow valve which is disposed on the side of the teeter totter opposite the liquid bladders.

14 Claims, 17 Drawing Figures

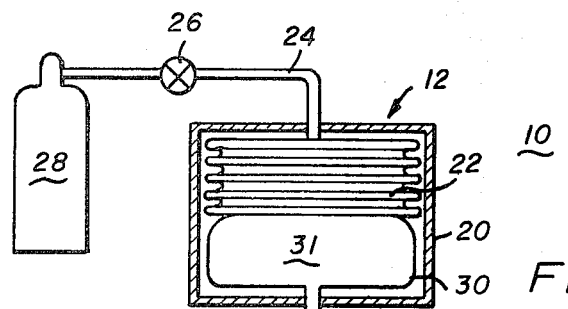
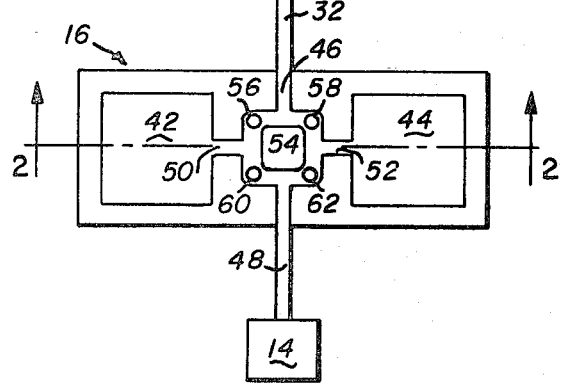
Fig_1
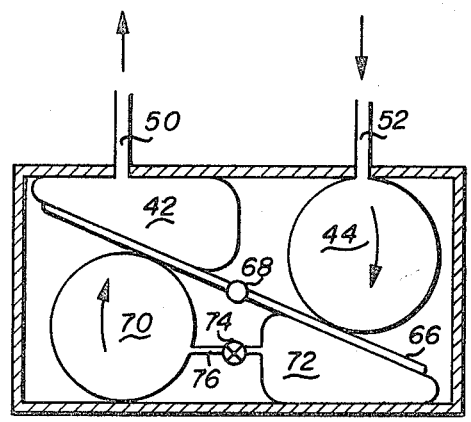
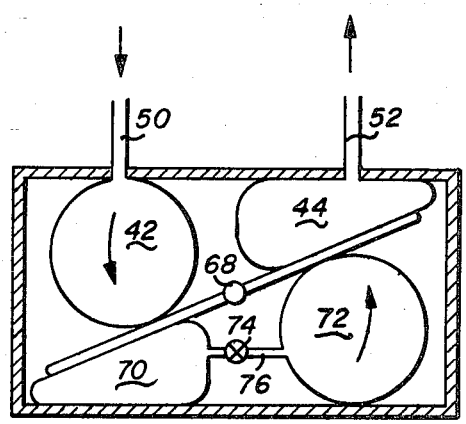
Fig_2A  Fig_2B
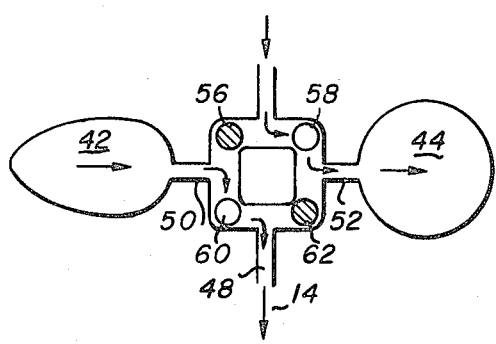
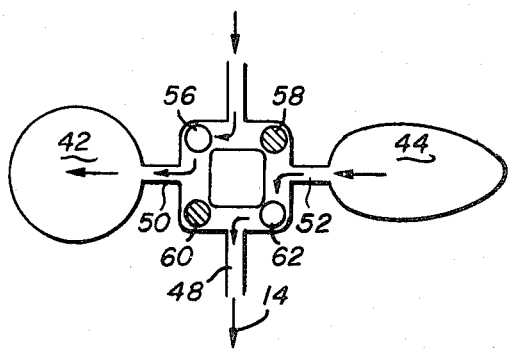
Fig_2C  Fig_2D

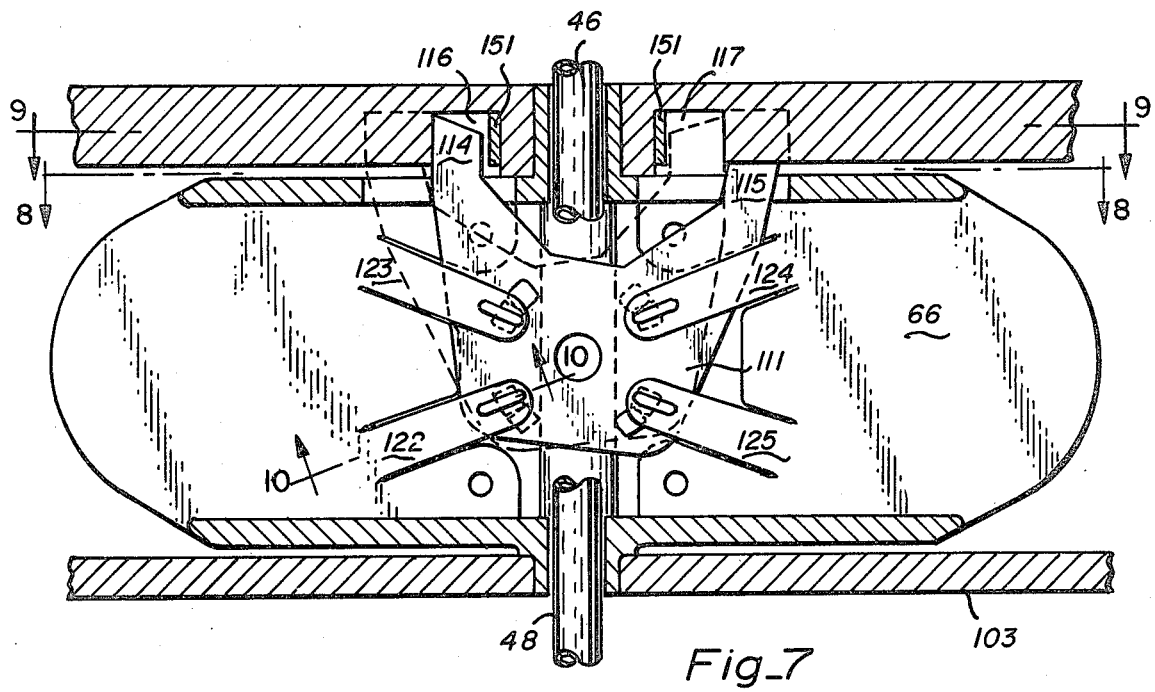
Fig_7
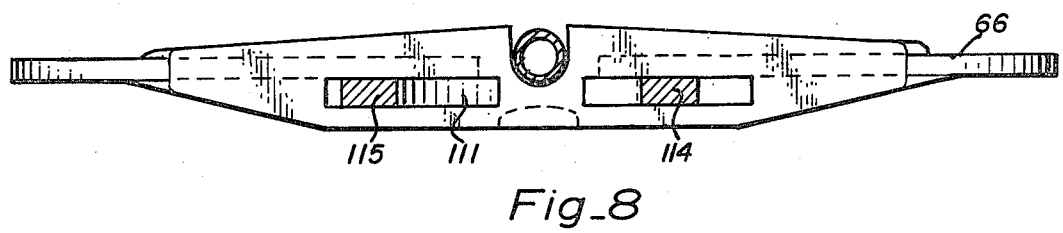
Fig_8
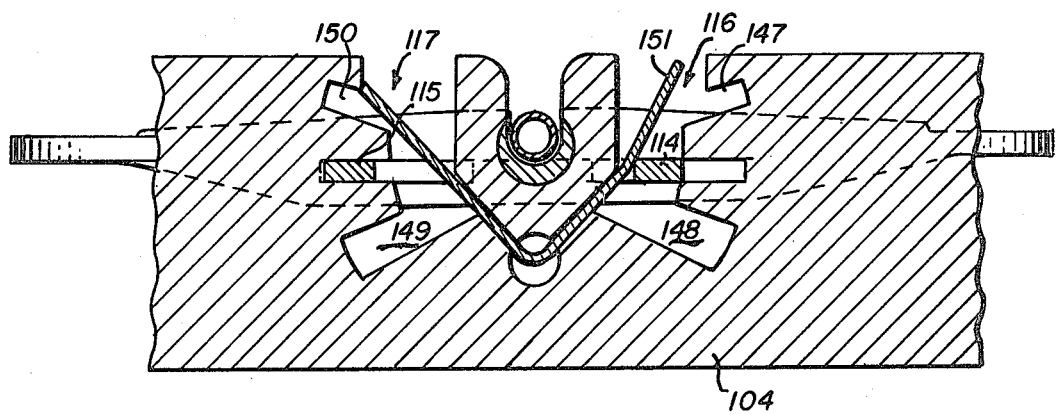
Fig_9

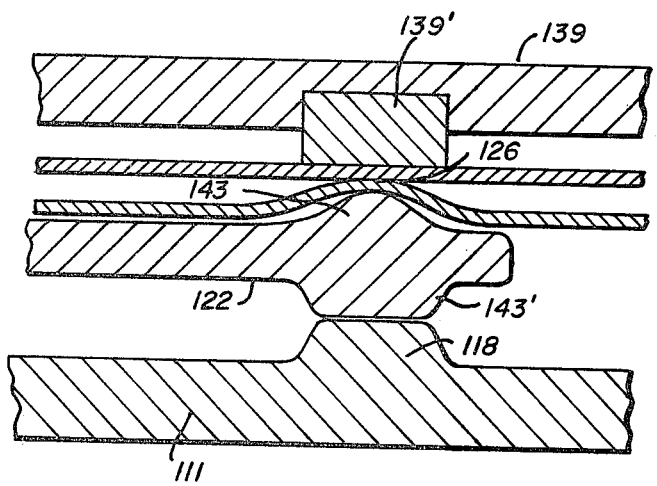
Fig_10
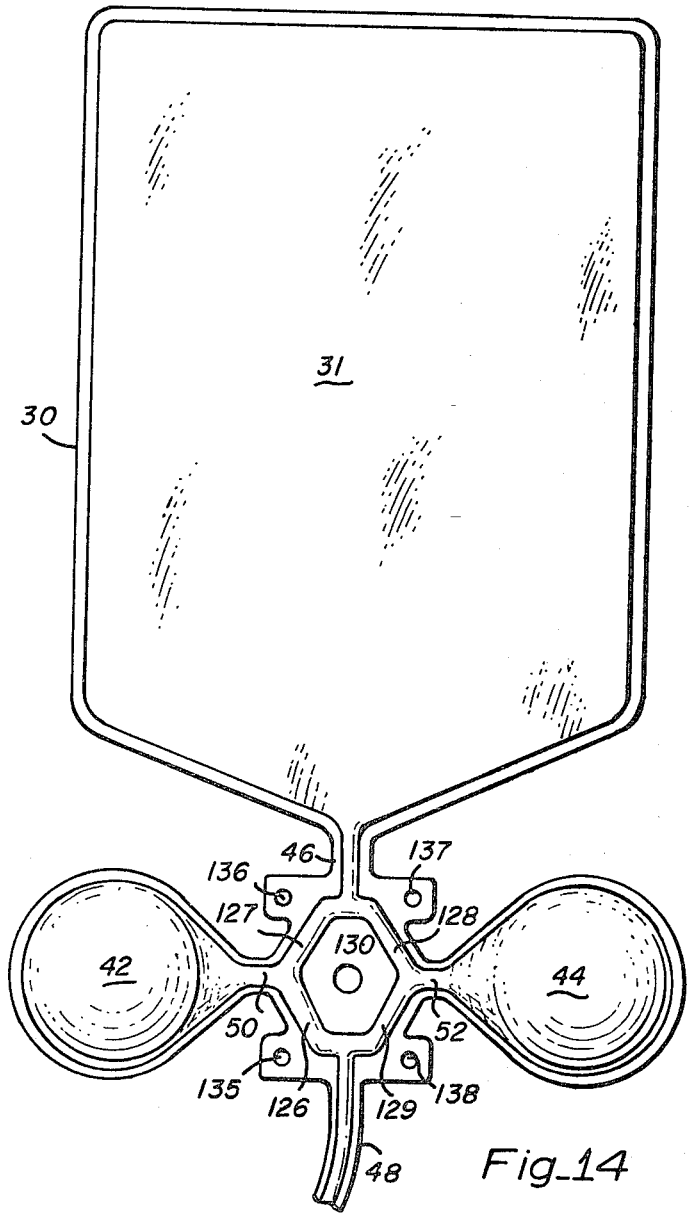
Fig_14

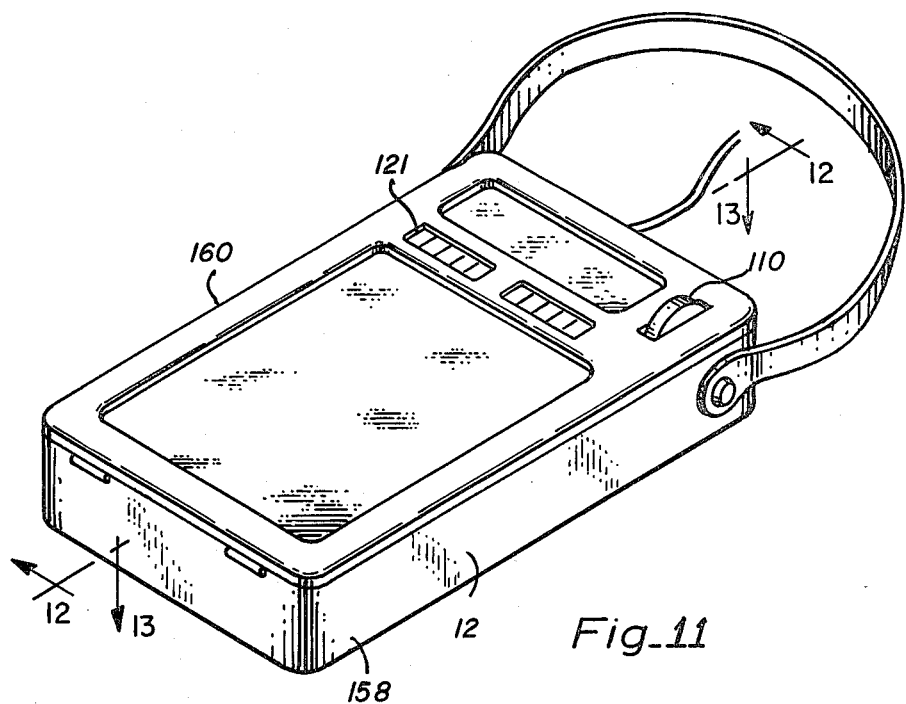
Fig_11
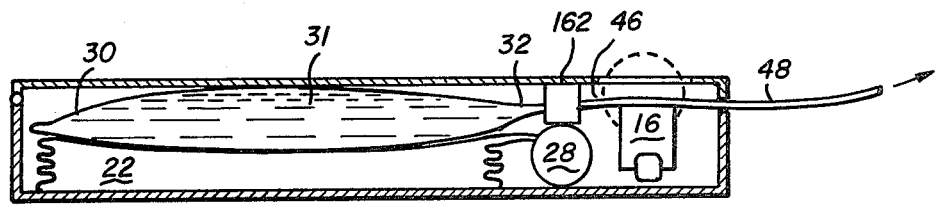
Fig_12
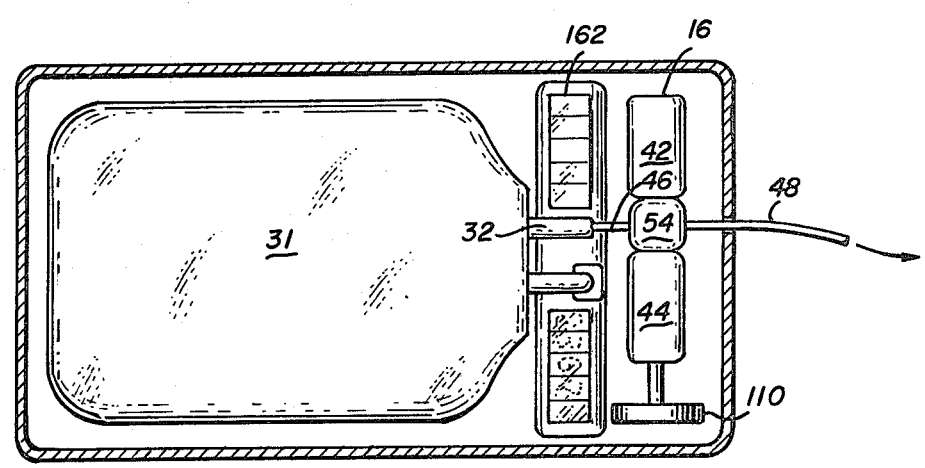
Fig_13

DEVICE FOR THE INTRAVENOUS OR ENTERIC INFUSION OF LIQUIDS INTO THE HUMAN BODY AT A PREDETERMINED CONSTANT RATE

BACKGROUND OF THE INVENTION

This invention relates to improvements in the administration of fluids to patients by means of lightweight and portable, yet highly accurate, fluid-metering and delivery devices.

The administration of fluids to patients is usually accomplished by gravity forces of the fluids from bottles and plastic bags suspended above the patient, whether it be for infusion in a vein or artery or through a naso-gastric or ostial tube into the gastrointestinal tract. The amount of pressure is varied depending upon the pressure head or the height from the bottle or bag of fluid to the inlet to the patient to overcome venous and/or arterial back pressure.

In order to control the amount of fluid entering the patient, restrictors, such as clamps, are placed on the inlet tubing and fluid is observed to drop from the fluid reservoir into a sighting tube. Drops are counted as the means for achieving some quantitative control. The larger the restrictor clamp tube opening is made, the greater the number of drops and thus the more fluid administered into the patient.

Thus, the above two elements of control have been the standard means for infusing fluid into a patient: pressure on the fluid and restrictors on the inlet tubing to control the amount of fluid administered.

The prior art has utilized these two modes to achieve reasonable levels of accuracy in administering fluids. A large number of devices have been made which elaborate on each of these modes. Pressurizing means have been devised as described in patents to Adelberg, U.S. Pat. Nos. 3,640,277 and 4,043,332 to Metcalf which disclose the use of gasses and liquids to pressurize the fluids to be administered. Also, a pressure cuff has been described to squeeze blood through a fixed diameter orifice. Reservoirs of carbon dioxide, air, and other gasses have been described as pressurizing means to squeeze the fluid to be administered and thus to overcome the need for hanging up the fluid to achieve the pressure head of gravity.

Still another group of pressure-driven devices utilizes portable electronic devices in the form of vests, such as described in U.S. Pat. No. 4,087,864, which allow for the solution bags to be carried by the patient and administered by electrically-driven or pressure-drive pumping devices.

All of the above proposed devices provide for complex electronic, electrical, mechanical or electromechanical devices and a number violate the currently accepted practice of the maintenance of sterility of the liquid from the fluid reservoir to the patient to reduce sepsis. Also a great emphasis has been placed in the above described prior art devices on the need for accuracy of administration, i.e., metering, thus incorporating into these devices highly complex means for achieving such accuracy. The commonly used mechanisms for metering volumes of fluid are by syringe types of dispensers, wherein a syringe is filled and expelled. These are referred to as volumetric pumps. Another commonly used mechanism is where a tube is rolled, the space in the tube being fixed in volume, the device being called a peristaltic pump, because of the wave-type action.

Other means for fluid metering have been proposed, such as in U.S. Pat. No. 3,292,824 to Arp et al and U.S. Pat. No. 3,370,759 to Johansson, which utilize a floating piston and various direction-changing devices.

All of these mechanisms incorporate moving parts, some of which touch the liquids to be administered, and most cannot meet stringent sterility requirements.

At the present time, a growing number of patients may now live on intravenous solutions for all of their lives, such as in the case of patients with the short-gut syndrome. Also, the introduction of new jejunostomy feeding tubes and new long-term nasogastric feeding tubes permits the carrying of fluids and the assumption of more normal modes of life, such as being able to go back to work, even though fluids are being administered. A number of patients can be ambulatory even though they are using cancer-chemotherapeutic drugs, anticoagulation drugs such as heparin, nutrients such as elemental diets and protein foods which avoid the necessity of using the body's normal digestive function. The need for a very simple, inexpensive, lightweight, yet accurate means of infusing liquids, will allow patients to leave the hospital at a great cost savings to society.

SUMMARY OF THE INVENTION

It is therefore a major object of the invention to provide a lightweight, portable, simple, and inexpensive device for infusing fluids into veins, arteries, and the gastrointestinal tract.

It is another object of this invention to provide a device which will supply pressurized fluids to patients at desired rates of infusion with acceptable accuracy.

It is still a further object of this invention to utilize the pressurizing liquid to be infused as the sole driving force to actuate a dispensing and metering device without the use of batteries or other energy sources, which will directly infuse into the patient desired quantities of material with a simple adjustment which can be made by the patient or the attendant.

It is still a further objective of the invention to provide a volumetric metering means which is driven by the pressure of the administration liquid itself.

It is also an object of this invention to provide a device for the intravenous and enteric infusion of a liquid into a human body which is portable, or lightweight, meters to an acceptable accuracy, is rugged, and allows the use of disposable, self-contained fluid systems.

It is also an object of this invention to provide a device for the intravenous or enteric infusion which utilizes a disposable fluid container which is sterilizable prior to use and which allows a sterile barrier to be maintained from and including the liquid directly to the needle or catheter through which the liquid is being administered into the patient.

It is still another object of the invention to provide a device for the intravenous or enteric infusion which combines the sterile, disposable metering means directly to the administration fluid container which can be shaped to various portions of the body to facilitate the wearing thereof by the patient comfortably over long periods of time and, thus, to normalize the patient's life. Such shapes, for example, may be in the form of a money-belt or a sleeve cuff or in an arm sling for long-term ambulatory application of chemotherapeutic agents.

Briefly, the present invention accomplishes the above stated, and many other, objects by utilizing a high-pressure source in the form of a spring plate or a pressure cartridge or the like and a pressure regulator set at a predetermined level to reduce the high pressure to a desirable operating pressure. The operating pressure is applied to a flexible pressurizing bladder in contact with a flexible liquid container to thereby pressurize the liquid to be administered to the patient. The high pressure source may also be a spring loaded pressure plate which presses against the flexible liquid container. The pressurized liquid is expelled into a metering means provided by two flexible liquid bladders which are alternately switched at a fixed predetermined volume so that as one fills with the pressurized liquid the other expels into the patient at a regulated pressure.

The metering means also includes means for controlling the rate at which the fluid volume is administered to the patient and how rapidly the liquid bladders change the flow of pressurized liquid into one or the other bladder. The latter means includes a pair of flexible damping bladders connected by an adjustable constant flow valve. The damping bladders are in pressure contact, either directly or indirectly, with the liquid bladders and expand or contract as the corresponding liquid bladder contracts or expands. There is also provided a teeter totter means which is pivoted between the pair of liquid bladders and which has the damping bladders on the side opposite to the liquid bladders. The teeter totter means rotates as a liquid bladder increases its size and includes the means to switch the connection between said liquid bladders.

BRIEF DESCRIPTION OF THE DRAWINGS

FIG. 1 is a diagrammatic representation of the device for the intravenous or enteric infusion in accordance with the present invention which is useful in explaining the operation thereof;

FIGS. 2A and 2B are diagrammatic cross-sectional representations taken along lines 2—2 of FIG. 1, and are likewise useful in explaining the principle of operation;

FIGS. 2C and 2D are plan diagrammatic representations of the metering means of the device illustrated in FIG. 1 and are likewise useful in explaining the operation of the present invention.

FIG. 7 is a top view of the teeter totter showing one position of the valve control element in solid lines and the other position of the valve control element in broken lines;

FIG. 8 is a cross-sectional view taken along line 8—8 of FIG. 7 showing the position of the valve control element in the teeter totter;

FIG. 9 is a cross-sectional view taken along line 9—9 of FIG. 7 showing the side wall cam following means;

FIG. 10 is an assembly, in cross section, of one "finger" of the teeter totter of FIG. 7 and valve 60 for explaining the operation of the crimping of the tube to open and close fluid flow.

FIG. 11 is a perspective view of the device for the intravenous or enteric infusion of the present invention showing one embodiment of either hand carrying or for shoulder strap application;

FIG. 12 is a cross-sectional view taken along line 11—11 of FIG. 10; and

FIG. 13 is a top view of the device of FIG. 10 with the top cover removed to show the arrangement of parts.

FIG. 14 is a plan view in cross section of the liquid container structure made in one piece with the metering structure.

DETAILED DESCRIPTION OF THE EMBODIMENT

Figure 3:
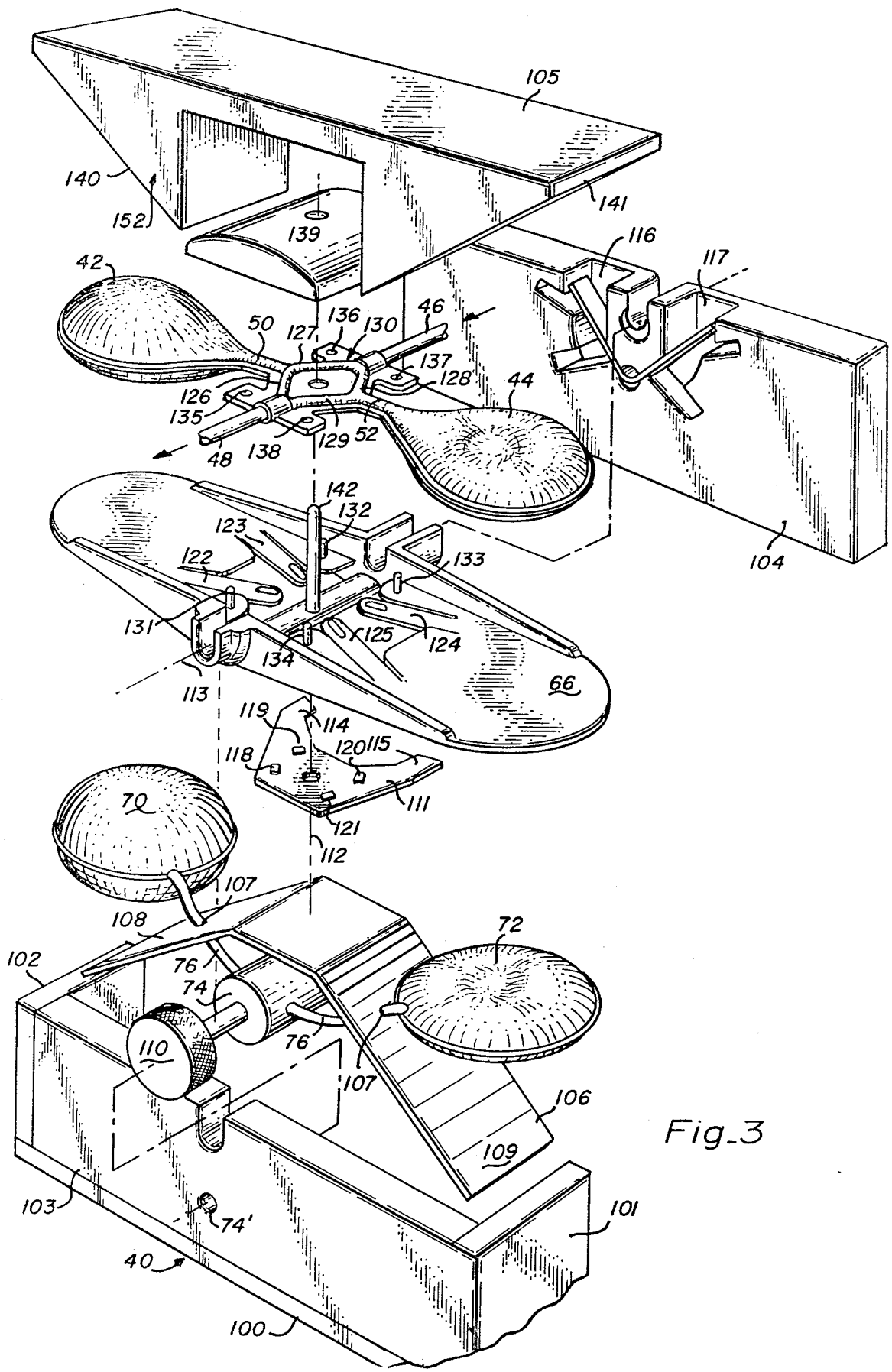
FIG. 3 is an exploded, perspective, partially broken away view of a preferred embodiment of the metering means of the device for the intravenous or enteric infusion of the present invention.

Referring now to the illustrated schematic representation of the device 10 for the intravenous and enteric infusion, in accordance with the present invention, it comprises a liquid storage means 12, a liquid discharge means 14, and a liquid metering means 16. The term "liquid", as used herein, refers to the material that is discharged into the patient by the device of the present invention and may be either liquid nutrient and/or liquid medicament. Further, even though the device of this invention will be described and its operation explained with particular emphasis to the infusion of a liquid into a patient, it has applications whenever it is desirable to dispense a liquid at a constant rate.

Liquid storage means 12 comprises a substantially rigid enclosure 20, and a flexible pressurizing bladder such as bellows 22 which is sealed with the exception of an inlet connected to tubing 24 through a convenient opening in enclosure 20. There is further provided a pressurized cartridge 28 which is connected to tubing 24 through a pressure regulator 26. Typically, cartridge 28 may contain a gas such as carbon dioxide under high pressure which is typically in the range of 1000 to 1200 psi. Pressure regulator 26 can be set to any desired output pressure and, by way of illustration for the application herein described, is set at a level of approximately 10 psi to pressurize bellows 22 with such a pressure.

Also contained in the enclosure 20 is a flexible liquid container 30 which houses a liquid 31 to be dispensed. Liquid container 30 is likewise sealed and is connected through exit port 32 via tubing to metering means 16 which in turn delivers pressurized and metered liquid to discharge means 14 which is usually, but not necessarily a filter and connected to tubing or a catheter or a hypodermic needle for well-known standard application to the patient.

Referring now to metering means 16, it comprises a pair of flexible liquid bladders 42 and 44 which are connected, respectively, through tubing 50 and 52 to a liquid distribution means 54. Distribution means 54 is also connected to exit port 32 and to discharge means 14. The entire metering means 16 is usually packaged into a housing 40 and pressurized liquid is applied to it via input port 46 from pressurizing means 12 and is expelled from it through tubing 48 to discharge means 14.

Referring now more particularly to distribution means 54, it is comprised of a rectangular configuration of tubing with restriction positions acting like a valve (referred to as "valve" hereafter and explained further below), such as valve positions 56, 58, 60 and 62, schematically represented at each of the corners. In this manner, each straight line section of distribution means 54 is connected, in the order stated, to exit port 32 through tubing 46 through which pressurized liquid is inserted into the metering means to tubing 50 to liquid bladder 42, to discharge means 14 through tubing 48 through which the liquid is expelled, and to tubing 52 to liquid bladder 44. Valves 56 and 62 are both closed when valves 58 and 60 are both open to fill bladder 44 and valves 56 and 62 are both open and valves 58 and 60 are both closed to fill bladder 42.

In connection with the explanation of the present invention, reference will be made to FIGS. 2A, 2B, 2C and 2D. FIGS. 2A and 2C illustrate the filling of bladder 44 hereafter referred to as the "first switching state" in which the pressurized fluid is forced into distribution means 54 through tubing 46 with valves 58 and 60 open and valves 56 and 62 closed. The pressurized fluid flows through tubing 52 into liquid bladder 44 and the fluid from liquid bladder 42 flows through tubing 50 to discharge means 14. Also shown is a teeter totter 66 which is pivoted about a pivot 68 midway between the bladders. Teeter totter 66 is rotated and pressed in a clockwise direction by expanding bladder 44, the teeter totter thereby exerts pressure on bladder 42 and expels liquid from that bladder through tubing 50 and open valve 60 into output tubing 48 to discharge means 14.

At this point, it should be understood that teeter totter 66 pressurizes liquid bladder 42 as the teeter totter rotates under the application of forces from explaining liquid bladder 44. As will be explained in connection with FIG. 3, teeter totter 66 also operates the means for switching valves 56, 58, 60 and 62 from filling bladder 44 to 42 and vice versa. For this purpose, teeter totter 66 is made responsive to angular position and when a preselected position is reached, a cam device, described below, switches the valves in such a manner that valves 56 and 62 are opened and valves 58 and 60 are closed.

FIGS. 2B and 2D represent the "second switching state". After switching to the second state, pressurized liquid flows from tubing 46 through open valve 56 into tubing 50 to fill liquid bladder 42. Expanding bladder 42 rotates teeter totter 66 in a counterclockwise direction to exert pressure on the previously filled liquid bladder 44 which then, in turn, will expel its volume of liquid through tubing 52 and open valve 62, to output tubing 48 and into discharge means 14. When the teeter totter reaches a certain angular position, the cam device again rotates and effects a change to the "first" position.

Referring, once more, to FIGS. 2A and 2B, there is also shown a damping means in the form of a pair of damping bladders 70 and 72 contained in housing 40 on the side of the teeter totter opposite to the side which is in contact with the pair of liquid bladders 42 and 44. Damping bladders 70 and 72 are also flexible bladders which are hermetically sealed except that they are connected to one another via an adjustable constant flow valve 74 and tubing 76. Valve 74 is in the nature of an adjustable throttle that controls the flow of fluid from bladder 70 to bladder 72 as illustrated in FIG. 2A, and from bladder 70 to bladder 72 as illustrated in FIG. 2B. The contents of bladders 70 and 72 may be referred to as the damping fluid and may either be a liquid or a gas, depending on the type of control valve 74 employed and on the desired degree of damping.

It should be clear at this time, and having particular reference to the situation depicted in FIG. 2A, that the pressurizing fluid in liquid bladder 44 is one factor in determining the force applied to liquid bladder 42 which expels the liquid into the patient and that the damping system is the other factor because there is an adjustable pressure drop across throttle 74. The smaller the pressure drop the greater will be the effect of the force exerted by liquid bladder 44 on liquid bladder 42 via the teeter totter.

The damping bladder system illustrated in FIG. 2 has been found most useful in providing such control. As liquid bladder 44 expands, it exerts a clockwise rotational force on the teeter totter 66 which is opposed by the damping fluid in damping bladder 72. No matter what the amount of pressure that is applied to fluid 31, within certain limits, rotation of the teeter totter is dependent on the damping fluid passing through control valve 74 into damping bladder 70 which thereby controls the amount of force applied by teeter totter 66 to liquid bladder 42 which dispenses the fluids to the patient. Accordingly, even though the pressure applied to fluid 31 may vary within a broad range, adjustment of valve 74 and thereby controlling the passage of damping fluid from damping bladder 72 to damping bladder 70, effectively allows metering of the fluid passing from liquid bladder 42 to the patient.

Thus, the rate at which the teeter totter may rotate is determined by the amount of damping fluid allowed to pass from side to side into bladders 70 and 72. By setting the volumes of the liquid bladders, the position of the teeter totter when it switches the valves from the "first" to the "second" position, and the size of the orifice in valve 74, the volume being dispensed into the patient over time can be made to be very accurate. With the size and shape of the bladders established and fixed and the teeter totter suitably switching over the position selected, the volume to the patient can be regulated entirely by the damping valve 74. There are many suitable damping means, one being a double acting piston and another being a spring which biases the teeter totter in a neutral position.

Referring now to FIG. 3 of the drawing, there is illustrated, an exploded view of a preferred embodiment of metering means 16 of the present invention. Whenever possible or appropriate, the same reference characters will be used in the description of the succeeding figures as were used in the description of the schematics of FIGS. 1 and 2 to designate like parts, even though the shape of the parts may be somewhat different.

Housing 40 of metering device 16 includes bottom 100, a pair of end walls 101 and 102 and a pair of side walls 103 and 104 which may all be interconnected with one another and which form an open housing covered by a cover 105. Disposed within housing 40 is a double inclined plate or lower anvil 106 which includes a pair of inclined portions 108 and 109, each having an opening 107 for tubing 76. Resting on top of inclined portions 108 and 109 are, respectively, a pair of flexible damping bladders 70 and 72 which are connected to one another through a constant flow valve 74 and tubing 76. Constant flow valve is provided with an adjustment knob 110 which allows for the convenient adjustment of the amount of fluid to be dispensed from outside of housing 40. Adjustment may also be made via a flexible cable from valve 74 to an adjustment knob at a remote location.

Pivoted above damping bladders 70 and 72 is teeter totter 66 to which a cam holding device 111 is mounted for oscillatory rotation about an axis 112 which is at right angles to teeter totter pivot axis 113. Cam device 111 has two actuating feet or portions 114 and 115 which move, one at a time in and out of channels 116 or 117, respectively, disposed in side wall 104 as will be explained hereinafter. Cam device 111 is provided with raised portions or tits 118, 119, 120 and 121 on its upper surface and teeter totter 66 is provided with flexible fingers 122, 123, 124 and 125 which have downwardly extending tits (shown in FIG. 10) which cooperate with the cam tits as will be explained hereinafter.

There is also provided an entirely sealed liquid system which comprises flexible liquid bladders 42 and 44 which are connected, respectively, through tubing 50 and 52 to a fluid distribution network which has tubular branches 126, 127, 128 and 129, and distribution network 130, in turn, is connected through tubing 46 to flexible liquid container 30 (not shown) and through tubing 48 to discharge means 14 (not shown). As best seen in enlarged FIG. 5, tubing 50 is connected to the junction of tubular portions 126 and 127, tubing 46 is connected to the junction of tubular portions 127 and 128, tubing 52 is connected to the junction of tubular portions 128 and 129, and tubing 48 is connected to the junction of tubular portions 129 and 126.

In a preferred embodiment of this invention, the sealed liquid system comprised of bladders 42 and 44, distribution network 130, container 13, dispenser 14, and tubing between these four portions are integral with one another so that the entire system can be sterilized and maintained in this condition for storage and use, as illustrated in FIG. 14. Further, this sealed system can be, and preferably is, of the disposable type so that it can be purchased for one time use, be inserted in the metering device of the present invention, and be discarded after use.

Another embodiment provides for the separate connection of metering unit 16 of FIG. 1 and liquid container 31 first prior to use.

Referring again to FIG. 3, teeter totter 66 is also provided with four locating pins 131, 132, 133 and 134 which cooperate with four locating openings 135, 136, 137 and 138 in liquid distribution network 130 to assure that the same is located for proper valving action as will hereinafter be explained. Upon placing fluid distribution network 130 into the metering device, the four openings in fluid distribution network 130 are placed over the locating pins so that pin 131 engages openings 135 and the other pins engage corresponding openings. Placed on top of distribution network 130 is a pressure pad 139 which may have individual pressure portions on its lower surface for better valving actions as shown in FIG. 10.

Figure 5:
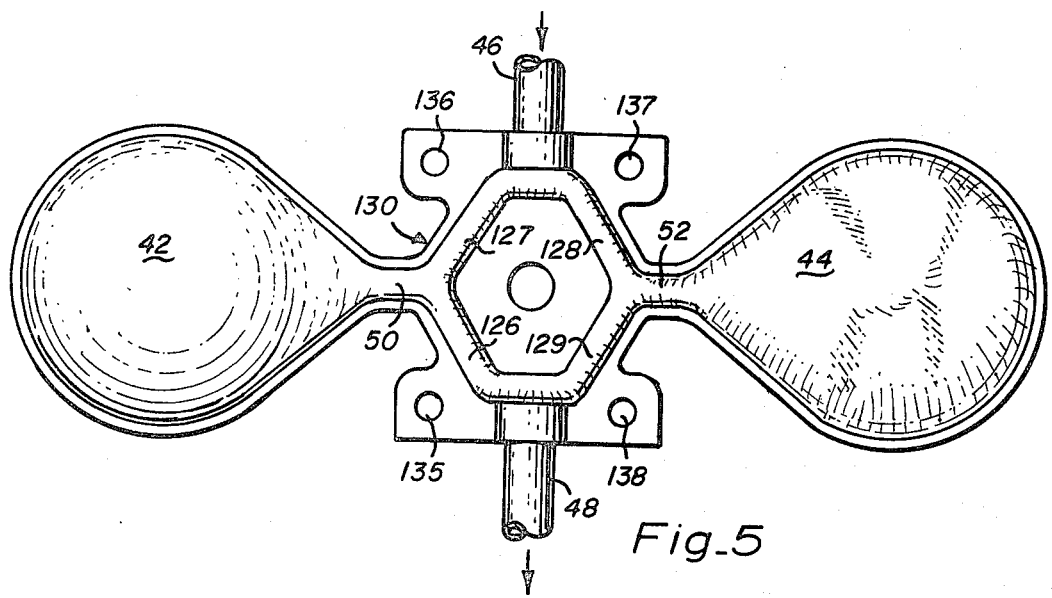
FIG. 5 is a top view of the disposable metering liquid bladders with discharge tube and input cut away.

Top or cover 105 is also provided with double inclined portions 140 and 141 to form an upper anvil 152. In assembly, lower anvil 106 is placed at the bottom of housing 40 with the adjustment shaft of throttle 74 passing through opening 74' in side wall 103 and anvil 106 resting on bottom 100. Damping bladders 70 and 72 are interconnected and placed on lower anvil 106. Teeter totter 66 with cam device 111 rotationally mounted thereto is placed in the U-shaped slots of side walls 103 and 104 so that the lower surface of the teeter totter rests on bladders 70 and 72. Thereafter, the fluid system portion shown in FIG. 5 is placed on the top of teeter totter 66 with the locating pins such as 131 engaging the openings in network 130 such as 135, and pad 139 is placed on shaft 142 and secured in place by some means such as a U-clip (not shown). Thereafter, upper anvil 152 is placed into housing 40 to close the same, its inclined portions resting on liquid bladders 42 and 44.

Figure 4:
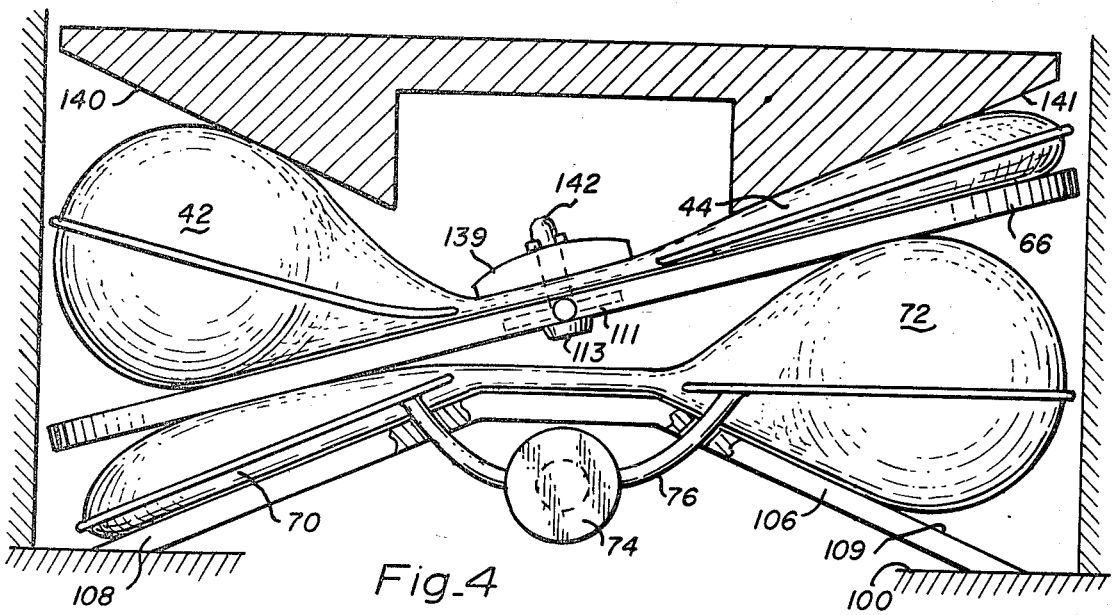
FIG. 4 is a side view of the metering means shown in FIG. 3 and illustrates an operational aspect thereof.

Referring now to the operation of the metering device of the invention, reference is made to FIGS. 3 to 10. As best seen in FIG. 4, which is a diagrammatic representation useful in employing the operation, as liquid bladder 42 expands against anvil surface 140, it rotates teeter totter 66 counterclockwise about axis 113 and compressed liquid bladder 44 against anvil surface 141 to expel liquid out of tubing 48. At the same time, damping bladder 70 is compressed between the lower surface of teeter totter 66 and lower anvil surface 108 which forces damping fluid through throttle 74 into expanding damping bladder 72 at a rate determined by throttle 74. Accordingly, the only rotational forces applied to teeter totter 66 is the expanding liquid bladder 42. Opposing this force are the damping bladders 70 and 72 and liquid bladder 44, the latter only to a negligible degree. Therefore, the rate of rotation of teeter totter 66, and therefore the rate or the amount of fluid applied to this discharge means, is primarily a function of throttle 74, the more open the throttle, the faster the rotation of teeter totter 66.

Figure 6:
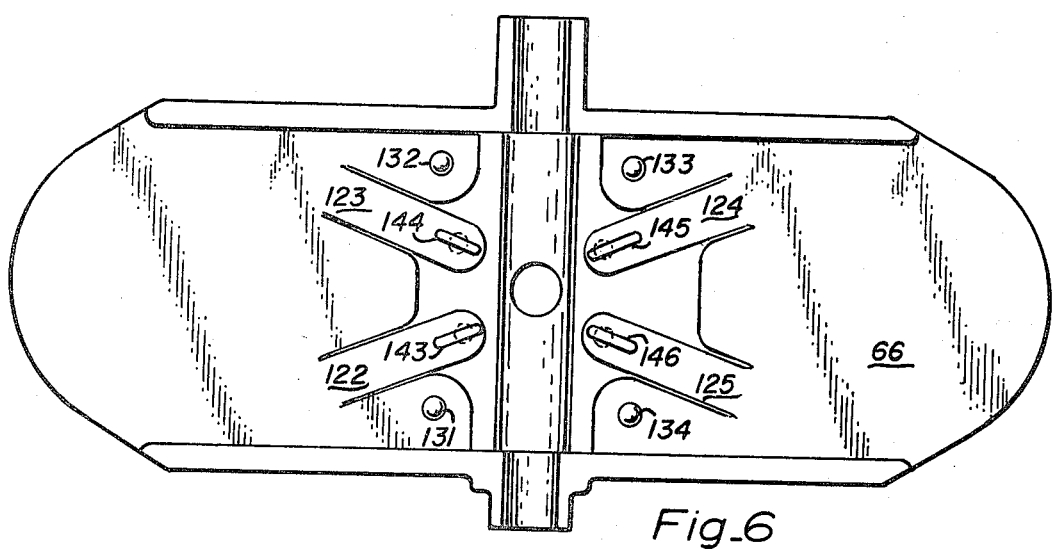
FIG. 6 is a top view of the teeter totter of FIG. 3.

Referring now to FIG. 6, there is shown an enlarged plan view of teeter totter 66 with fingers 122, 123, 124, and 125. Each finger is further provided with a knob or tit 142, 144, 145 and 146 which directly engage tubular portion 126, 127, 128 and 129, respectively, as cam device 111 is either in the first position or in the second position. Similar kinds of knobs or tits may be placed on the underside of each finger and these will be identified in FIG. 10 by the same reference character as the tit on top of the finger.

Referring now to FIG. 10 of the drawing, there is shown, in cross section of an example, one portion of the valving system for closing and for opening tubular portion 126 of FIG. 5. It should be understood that tubular portion 126 and 128 form one pair that are closed and opened simultaneously and that tubular portion 127 and 129 form another pair that are closed and opened simultaneously and that when one pair is open, the other pair is closed. In the "first" position, liquid bladder 44 is filled, and that in the "second" position liquid bladder 42 is filled. Accordingly, in the "first" position tubular portions 127 and 129 are closed and in the "second" position, tubular portions 126 and 128 are closed. The explanation that follows is applicable to the closing and opening of all valves even though only valve 60 opening and closing tubular portion 126 is shown. When cam device 111 rotates from the first position to the second position, tit 118 on the upper surface of cam device 111 is rotated into engagement with tit 143' on the underside of flexible finger 122 to raise the finger in an upward direction causing its tit 143 on its upper surface to pinch into tubular portion 126 as it is urged against pad 139 to close the same and prevent the flow from going therethrough. As cam device 111 is rotated into the second position, tit 118 is rotated out of engagement with tit 143' so that finger 122 assumes its normal horizontal position to thereby open tubular portion 126 to normal fluid flow which corresponds with valve 60 being open.

FIGS. 7, 8 and 9 show the operation of cam device 111 which controls valves 56, 60, 62 and 64. For the sake of simplicity, only the parts essential to the valve operation are shown. As already mentioned, side wall 104 is provided, on its inner surface, with a channel 116 on one side and a channel 117 on the other side disposed within the channels is a single leaf spring 151 which exerts an outward bias, i.e., a bias to the outer channel wall, on anything moving upwards in the channel. Further, each channel is provided with a pair of radial slots, shown as 147, 148, 149 and 150 which are centered more or less about teeter totter pivot axis 113 and which extend outwardly from the channel a distance to allow operative portions or feet 114 and 115 of cam 111 to move or fall into them as the teeter totter moves between its first and second position.

FIG. 7 shows teeter totter 66 rotating clockwise from the first to the second position so that cam device 111 is in the first switching state and liquid bladder 44 is filling and fingers 123 and 125 close the overlying tubular portions 127 and 129. This is shown in solid outline and foot 115 rides on the inner surface of side wall 104 as foot 114 rides upwardly in channel 116 and against spring 151. As foot 114 reaches slot 147, leaf spring 151 will force 114 into slot 147, thus rotating cam device 111 counterclockwise as viewed in FIG. 7 and will cause foot 115 to enter shot channel 117 through slot 149, thereby assuming the second switching state and closing tubular channels 128 and 126. The fluid under pressure then fills bladder 42 and the teeter totter now reverses its direction of rotation and will rotate counterclockwise with foot 114 now riding on the inner surface of side wall 104 and foot 115 riding upwards in channel 117 against spring 151. Cam device 111 in the second switching position is shown in dashed line outline. The teeter totter will continue its counterclockwise rotation and fill liquid bladder 42 until foot 115 reaches slot 150 and foot 114 reaches slot 148 at which time spring 151 will kick cam device 111 from its second position to its first position to once more start filling bladder 44 as shown in FIG. 2A.

Referring now to FIGS. 11, 12, and 13, there is shown a convenient package for the device for the intravenous or enteric infusion of the present invention. The package comprising a housing 158 having a cover 160 can be opened to provide access to the interior. Disposed inside housing 158 is a standard one liter, or one-half liter, plastic intravenous or enteric solution bag 40 which corresponds to container 30 shown in the previous figures and which houses the liquid 31 to be dispensed. Also disposed within the housing and placed below the liquid container is flexible pressurizing bladder 22 and pressurizing cartridge 28, to which it is connected through a pressure regulator not shown and through tubing 24. The exit port of container 30 is connected to a metering device 16 through tubing 46 and the output of metering device 16 is connected, via tubing 48 to a utilization device, not shown. A control knob 110 is allowed to project through cover 160 so that is may be adjusted from outside the housing to set the desired rate of the teeter totter through control of the damping valve 74. The device is further provided a counter 162 which may be connected to the oscillating teeter totter to record the times direction is changed and thus how much liquid was infused into the patient or how much has yet to be infused.

Metering device 16 is shown in schematic form only in FIG. 13 having liquid bladders 42 and 44 and a distribution network 54 interconnecting these bladders with one another and with the container 30 and discharge tubing 48.

It should be understood that teeter totter 66 primarily performs the function of operating the valves controlling the flow of fluid through the distribution network 54 when a certain volume is reached in one of the liquid bladders. Teeter totter 66 does not actually control the rate at which the fluid is metered through device 16 since bladder 44 may be placed directly in contact with bladder 72 and bladder 42 may be placed directly in contact with bladder 70 to achieve the same or a similar result in the absence of the tetter totter. It should also be understood that the four flexible bladders 42, 44, 70 and 72 may be replaced by a pair of cylinders with a double acting piston. More particularly, bladders 42 and 70 may be replaced with a cylinder having a double action piston, the upper portion of the cylinder replacing bladder 42 and the lower portion of the cylinder replacing bladder 70. Similarly, bladders 44 and 72 may be formed in the cylinder space on appropriate sides of a double action cylinder. In such an arrangement, the lower portions on the cylinder are connected through a throttle and the upper portions of the cylinder are interconnected through a fluid distribution network, including valving means. For actuating the valving means, cylinder position may be utilized.

What is claimed is:

1. A device for the intravenous and enteric infusion of a liquid into a human body at a predetermined average rate comprising:
storage means for holding the entire amount of said liquid to be infused, said storage means including an exit port through which said liquid is expelled;
gaseous pressurizing means for pressurizing said liquid in said storage means and for maintaining and expelling said liquid at a substantially constant predetermined pressure;
discharge means adapted for expelling said liquid into the body, said discharge means being passive; and
active metering means connected between said exit port and said discharge means, said metering means being actuated solely by said pressurized liquid and being operative to deliver a predetermined average amount of said liquid per unit time to said discharge means.

2. A device in accordance with claim 1 in which said storage means includes a flexible container for liquids connected to said exit port for holding said liquid, said liquid being pressurized by pressurizing said flexible container with said pressurizing means.

3. A device in accordance with claim 2 in which said pressurizing means includes a pressurizing bladder and a source of a pressurized fluid connected to said pressurizing bladder, said pressurizing bladder being disposed in pressure contact with said container for liquids to pressurize said container.

4. A device in accordance with claim 3 which said storage means further includes a substantially nonflexible enclosure, and in which said flexible liquid container and said pressurizing bladder are disposed within said enclosure, said enclosure being dimensioned such that as said pressurizing bladder is pressurized and tends to increase its volume, the volume of said liquid container is pressurized from the outside by said pressurizing bladder which tends to decrease its volume to thereby pressurize said liquid.

5. A device in accordance with claim 3 in which a pressure regulator is connected between said source of pressurized fluid and said pressurizing bladder to maintain the pressure in said pressurizing bladder substantially constant.

6. A device in accordance with claim 5 in which said pressurizing bladder is in the form of a bellows having a portion in pressure contact with said liquid container.

7. A device in accordance with claim 1 in which said metering means includes a pair of substantially identical flexible liquid bladders each having an opening, liquid distribution means connected between the openings of said liquid bladders and said exit port and said discharge means, valve means disposed in operative relationship with said liquid distribution means, and valve control means operatively associated with said valve means for alternating between a first switching state in which one liquid bladder is connected to said exit port and the other liquid bladder is connected to said discharge means and a second switching state in which said one liquid bladder is connected to said discharge means and said other liquid bladder is connected to said exit port, whereby one liquid bladder is filled with said liquid from said liquid container while the other liquid bladder is emptied into said discharge means.

8. A device in accordance with claim 7 in which said valve control means includes volume sensing means responsive to the volume of said liquid bladders and operative to change from one to the other switching state when one of said bladders reaches a predetermined volume.

9. A device in accordance with claim 1 in which the storage means is shaped in the form and forms part of a belt for wearing around the waist.

10. A device for the intravenous and enteric infusion of a liquid into a human body at a predetermined average rate comprising:
   (a) storage means for holding said liquid, said storage means including, an exit port through which said liquid is expelled and means for forcing said liquid through said exit port at a substantially constant predetermined pressure;
   (b) discharge means adapted for expelling said liquid into the human body, said discharge means being passive; and
   (c) metering means connecting between said exit port and said discharge means, said metering means being actuated solely by said forced liquid and being operative to deliver a predetermined average amount of said liquid per unit time to said discharge means, said metering means including:
      (1) a pair of flexible liquid bladders, each bladder having an opening,
      (2) liquid distribution means connected between said openings in said liquid bladders and said exit port and said discharge means,
      (3) valve means disposed in operative relationship with said liquid distribution means,
      (4) valve control means operatively associated with said valve means for alternating said valve means between a first switching state in which one liquid bladder is connected to said exit port and the other liquid bladder is connected to said discharge means, and a second switching state in which said one liquid bladder is connected to said discharge means and said other liquid bladder is connected to said exit port, and
      (5) volume sensing means including a teeter totter means pivoted for rotation about an axis between said liquid bladders, said teeter totter means having end portions which are cooperatively disposed adjacent said bladders so that the end portion adjacent the expanding liquid bladder rotates said teeter totter means to cause the other end portion to pressurize and contract the other liquid bladder, said valve control means being responsive to said volume sensing means and operative to change from one to the other of said switching state when a liquid bladder reaches a predetermined volume.

11. A device in accordance with claim 10 in which said metering means includes a damping means responsive to the change in liquid bladder volume and operative to maintain said rate of change at a predetermined rate of change.

12. A device in accordance with claim 11 in which said damping means includes, a pair of flexible damping bladders, a damping fluid within said damping bladders, and an adjustable constant flow valve connected between said damping bladders for controlling the flow of damping fluid between said damping bladders, said damping bladders being disposed such that each one is in pressure contact with a liquid bladder to control the rate at which said liquid bladders change their respective volumes.

13. A device in accordance with claim 10 in which said metering means further includes a damping means, said damping means having a pair of flexible damping bladders containing a damping fluid and an adjustable constant flow valve for said damping fluid connecting between said damping bladders, said pair of damping bladders being disposed on the side of said teeter totter means opposite to said pair of flexible liquid bladders so that the rate of rotation of said teeter totter means is damped by said damping bladders which act in opposition to the expanding liquid bladder connected to said exit port.

14. A device in accordance with claim 10 in which said teeter totter includes cam means responsive to the inclination of said teeter totter and operative to actuate said valve control means to switch between said first and said second switching state at preselected inclinations.

* * * * *